(12) United States Patent
Moulden et al.

(10) Patent No.: US 9,415,174 B2
(45) Date of Patent: Aug. 16, 2016

(54) SUCTION REGULATOR HAVING FOUR MODES OF OPERATION

(71) Applicant: Boehringer Laboratories LLC, Phoenixville, PA (US)

(72) Inventors: Steven C. Moulden, West Chester, PA (US); John Karpowicz, Chester Springs, PA (US); Allison Lloyd, Norristown, PA (US); Kevin P. Klocek, Wynnewood, PA (US)

(73) Assignee: Boehringer Technologies, LP, Phoenixville, PA (US)

( * ) Notice: Subject to any disclaimer, the term of this patent is extended or adjusted under 35 U.S.C. 154(b) by 206 days.

(21) Appl. No.: 14/457,728

(22) Filed: Aug. 12, 2014

(65) Prior Publication Data

US 2015/0088068 A1    Mar. 26, 2015

Related U.S. Application Data

(60) Provisional application No. 61/881,744, filed on Sep. 24, 2013.

(51) Int. Cl.
*A61M 5/48*    (2006.01)
*A61M 1/00*    (2006.01)

(52) U.S. Cl.
CPC ............... *A61M 5/48* (2013.01); *A61M 1/0033* (2014.02); *A61M 1/0037* (2013.01); *A61M 1/0058* (2013.01); *A61M 5/482* (2013.01); *A61M 1/0062* (2013.01); *A61M 5/484* (2013.01); *A61M 5/486* (2013.01); *A61M 5/488* (2013.01)

(58) Field of Classification Search
CPC ..... A61M 5/48; A61M 1/0058; A61M 5/482; A61M 5/484; A61M 5/486; A61M 5/488; A61M 1/0062; A61M 1/0068; A61M 5/36; A61M 5/365; A61M 1/0033; A61M 1/0037
USPC .......... 604/118–123, 131, 140, 146, 149, 151
See application file for complete search history.

(56) References Cited

U.S. PATENT DOCUMENTS

| | | | | |
|---|---|---|---|---|
| 4,988,336 | A * | 1/1991 | Kohn | A61M 1/0049 604/119 |
| 5,599,308 | A * | 2/1997 | Krupa | A61M 1/0037 604/118 |
| 5,992,239 | A | 11/1999 | Boehringer et al. | |
| 6,228,056 | B1 | 5/2001 | Boehringer et al. | |
| 7,143,773 | B2 * | 12/2006 | Stinson | G05D 16/0636 137/1 |

* cited by examiner

*Primary Examiner* — Manuel Mendez
(74) *Attorney, Agent, or Firm* — Caesasr Rivise, PC

(57) ABSTRACT

A suction regulator arranged to be coupled to a source of partial vacuum and a patient circuit and which is operative in four modes is disclosed. A first mode isolates the source of partial vacuum from the patient. A second mode provides continuous regulated suction to the patient. A third mode provides intermittent regulated suction to the patient. The fourth mode provides unregulated full suction to the patient. The regulator includes a movable control knob for establishing the first, second, third and fourth modes and a detent mechanism holding the control knob in the position to select the desired mode. An interlock is also provided to prevent the control knob from being accidentally moved to the position establishing the unregulated full suction mode.

20 Claims, 7 Drawing Sheets

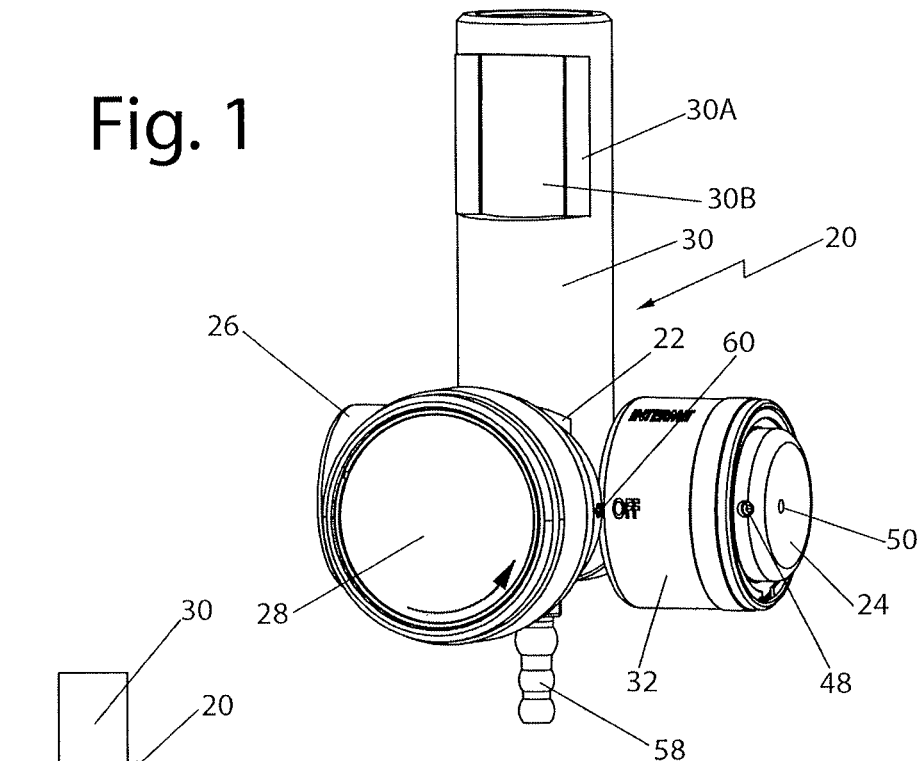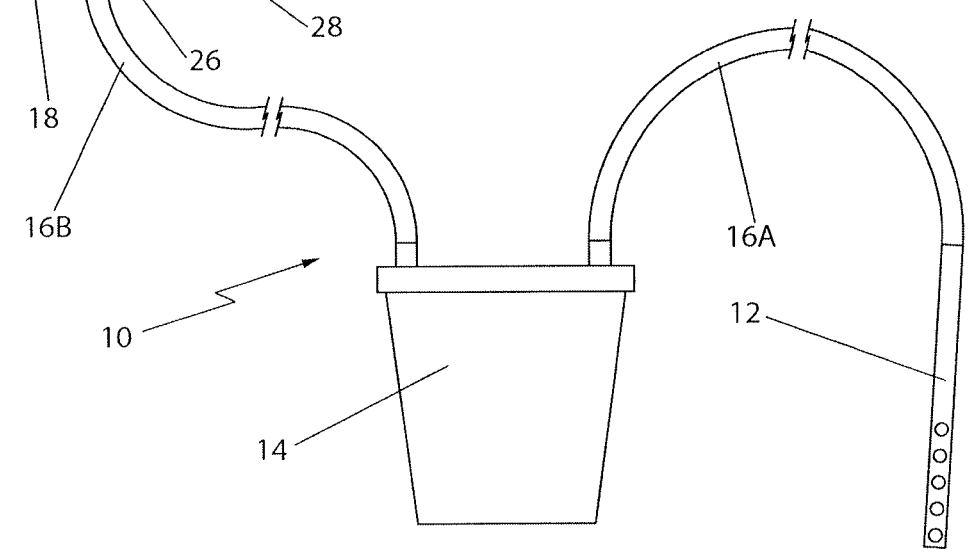

"OFF" MODE

"CONT" MODE

"LINE" MODE

"INTERMIT" MODE "OFF" PHASE

"INTERMIT" MODE "ON" PHASE

SUCTION REGULATOR HAVING FOUR MODES OF OPERATION

CROSS-REFERENCE TO RELATED APPLICATIONS

This utility application claims the benefit under 35 U.S.C. §119(e) of Provisional Application Ser. No. 61/881,744, filed on Sep. 24, 2013 entitled Suction Regulator Having Four Modes Of Operation, whose entire disclosure is incorporated by reference herein and which is assigned to the same assignee as the subject invention.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISK

Not Applicable

FIELD OF THE INVENTION

The disclosed invention relates to devices for a medical fluid aspiration systems and more particularly to intermittent suction regulators.

BACKGROUND OF THE INVENTION

Suction controls are routinely used in hospitals to regulate the level of suction delivered from a central supply system to the patient. Patient safety requires the high vacuum from the central supply be regulated to a lower safe level and adjustable for any number of clinical needs. On its most basic level, suction is used to remove fluids and debris from body cavities and is employed in virtually any location where a patient is present. Modern hospitals employ central suction systems with distributed supply at the patient bed. Mechanical controls reduce the high vacuum levels present in the central suction system to lower levels safe for patients and suitable for the patient collection devices. Collection devices are typically plastic, disposable devices that are used to accumulate fluids and debris. The collection devices are located between the point of collection and the control device and serve to protect the piping system and manual controls from contamination by bodily substances.

The manual controls that interface high vacuum in the central suction system with the patient contact collection systems are typically reusable, mechanical devices. The construction of these devices makes them prone to retention of fluids that may harbor infectious agents. Unlike other fluidic systems in the hospital, such as oxygen, nitrogen, or medical air, the inlet to the suction system is proximal to the patient and may not be filtered. In addition to room air, caregivers unintentionally introduce foreign material into the flow paths of these devices. The devices also contribute to contact vectors for contamination.

A complete fluid aspiration device consists of a control or regulator that attaches to the hospital central suction system, e.g., a system for providing partial vacuum at a desired level, for applying safe levels of suction pressure, collection devices for the accumulation of fluids and air separation, tubing and patient contact items, such as a catheter or a collection wand.

Suction controls may require a safety mechanism that is unique to the clinical application. For example, gastric drainage typically employs an intermittent cycling of the suction pressure to guard against continual application of suction to the interior of the gastric space which could result in traumatic lesions and possibly bleeding. In particular, in evacuating fluids from the stomach area it is possible for the suction catheter to engage the stomach wall, thereby occluding the inlet of the suction catheter. In such event, it is desirable to have the vacuum draw of fluid from the stomach become discontinuous, to free the catheter from sucking against the stomach wall and damaging the stomach lining. It is also common for debris in the stomach area to occlude the inlet ports of a catheter and thereby restrict or impede fluid flow. Periodic and regular relief of suction pressure to atmosphere will discourage debris accumulation on catheter inlets. Because it is not always readily apparent when such occlusion occurs, suction regulators can be operated on a substantially ongoing or intermittent manner by periodic regular cycling of vacuum on and venting to atmosphere of the collection circuit. In other instances, intermittent regulators are provided that may be set to operate in either a continuously intermittent (on/off, on/off, on/off, etc.) mode, or may be capable of being set to optionally operate in a constant-on or in a constant-off mode. It is also known that because of the nature of fluids being withdrawn from the body of a patient, it is necessary to provide regulators that are capable of being sterilized between uses.

In U.S. Pat. No. 6,228,056, whose disclosure is specifically incorporated by reference herein, and which is assigned to Boehringer Laboratories, Inc., the same assignee as the subject invention, there is disclosed and claimed an intermittent suction regulator, which is among other things particularly suited for gastric evacuation applications. That regulator includes a control mechanism for controlling the intermittent time cycle, with the control mechanism being isolated from the body fluids that are delivered to the regulator from the body of the patient.

Boehringer Laboratories, Inc. offers various suction regulators, some of which are constructed in accordance with its aforementioned patent. Those commercially available regulators also have three modes of operation. Those modes are: the "OFF" mode; the "CONTINUOUS" mode; and the "INTERMITTENT" mode. In the "OFF" mode the line that is coupled to the patient is isolated from the hospital's suction line and is thus at the ambient atmospheric pressure. In the "CONTINUOUS" mode the line that is coupled to the patient is at a regulated level of suction (e.g., 200 mm Hg.) that is provided continuously and is below the level of suction (e.g., 600 mm Hg.) provided by the hospital's suction line. In the "INTERMITTENT" mode the line that is coupled to the patient is at a regulated level of suction (e.g., 200 mm Hg.) but is provided intermittently, e.g., 16-20 seconds "on" and 8-10 seconds "off".

While the intermittent regulators of the foregoing patents and those commercially available from Boehringer Laboratories, Inc. are eminently suitable for their intended purposes the never-the-less leaves something to be desired from the standpoint of functionality. In particular, for some applications, it may be desirable to enable the suction regulator to apply the full suction available on the hospital's suction line, e.g., 600 mm Hg., to the line to the patient. For example, if a device which is connected in the patient's suction line should become clogged, it may be desired to apply the full suction to that line to clear the device. Accordingly, a need exists for an intermittent suction regulator which also provides a mode of operation in which the full vacuum provided at the hospital's suction line is coupled to the patient's line. The subject invention addresses that need. In addition, hospitals and other similar institutions often desire standardization. Thus a suction regulator that satisfies all clinical needs would be welcome addition. The subject invention addresses that need as well.

SUMMARY OF THE INVENTION

In accordance with one aspect of this invention there is provided a regulator for regulating suction provided via a line to a patient circuit, e.g., as part of a system for accomplishing the vacuum withdrawal of body fluids from the patient. The regulator basically comprises a housing having an inlet and an outlet. The inlet is arranged to be coupled to a source of partial vacuum, e.g., a hospital's vacuum line. The outlet is arranged to be coupled to the patient circuit, e.g., to a container for receipt of body fluids from the patient. The regulator is arranged for operating in any one of four discrete modes of operation. A first one of the modes isolates the source of partial vacuum from the patient circuit. A second one of the modes provides continuous regulated suction to the patient circuit, with the continuous regulated suction being limited to a level below the level of partial vacuum provided from the source of partial vacuum. A third of the modes provides intermittent regulated suction to the patient circuit, with the intermittent regulated suction being limited to a level below the level of partial vacuum provided from the source of partial vacuum. A fourth of the modes provides continuous full suction to the patient circuit, with the continuous full suction being at the level of suction provided by the source of partial vacuum.

In accordance with one preferred aspect of this invention the regulator includes a control member arranged to be moved to one of four discrete positions, each corresponding to a respective one of the four modes of operation. The regulator is arranged, e.g., it includes an interlock, to prevent the control member from being accidentally moved to the position corresponding to the fourth mode of operation. The regulator also includes a detent mechanism to hold the control member in any one of its first, second or third discrete positions.

BRIEF DESCRIPTION OF THE DRAWING FIGURES

FIG. 1 is an isometric view of one exemplary embodiment of a suction regulator having four modes of operation and which is constructed in accordance with this invention shown in its "OFF" mode of operation;

FIG. 2 is a schematic illustration of the suction regulator shown in FIG. 1 in use in an exemplary system for withdrawing body fluids from a patient, with the regulator being shown connected to a source of partial vacuum, e.g., a hospital's suction line;

Figure 6:
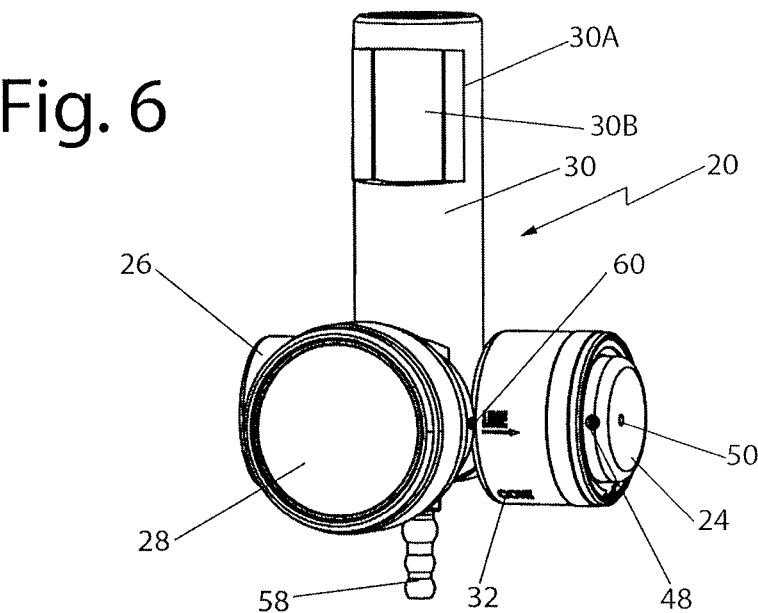
FIG. 6 is a reduced isometric view of the suction regulator of FIG. 1 shown in its "LINE" mode of operation, wherein full suction available from the source of partial vacuum, e.g., a hospital's suction line, is provided to the patient's line.
Figures 8, 9:
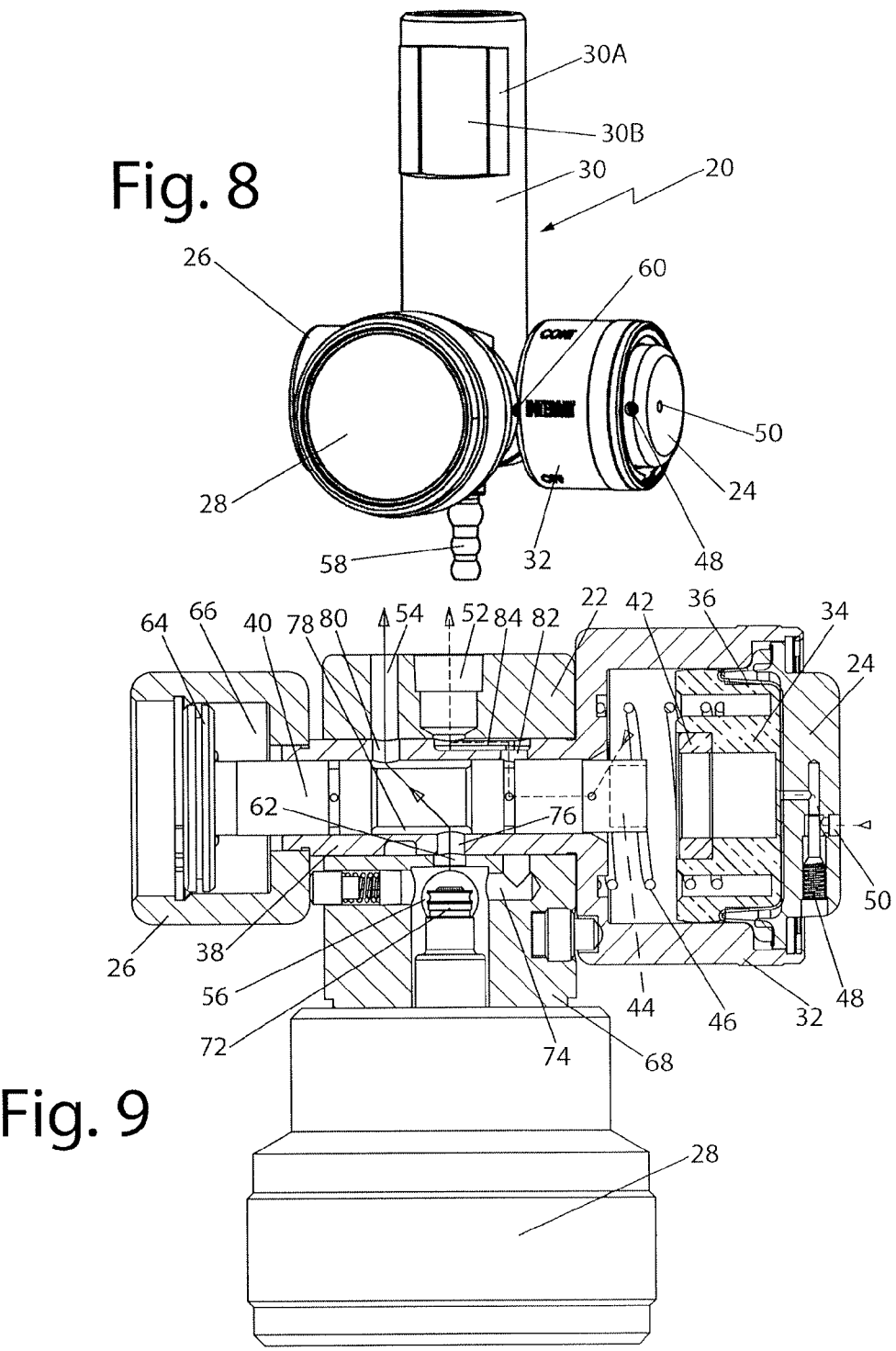
Figure 10:
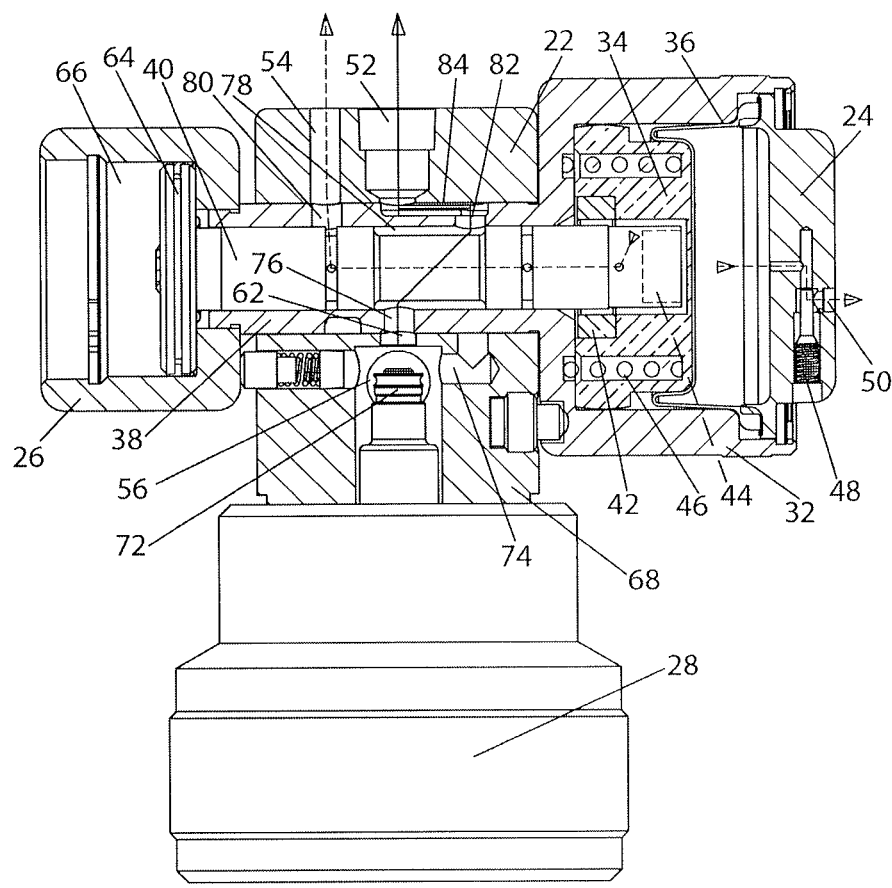
Figure 11:
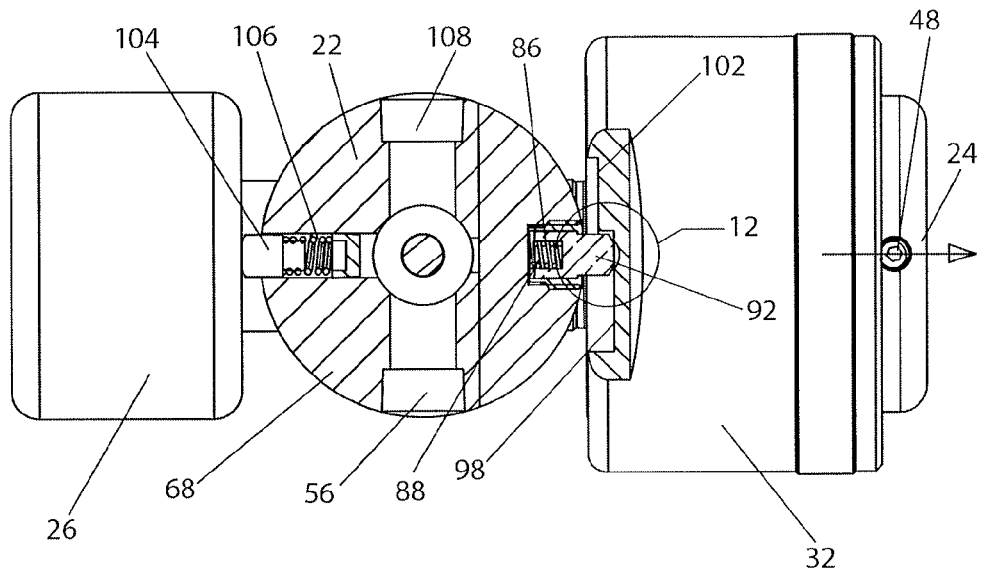
Figure 12:
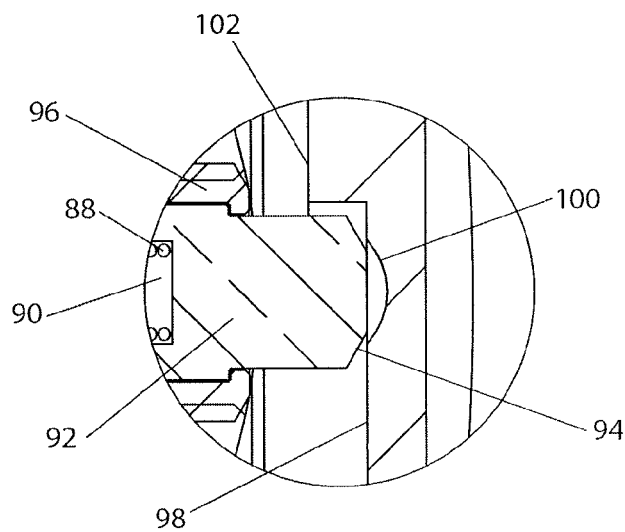

FIG. 8 is a reduced isometric view of the suction regulator shown in its intermittent (INTERMIT") mode of operation wherein the regulator cycles through two phases, one of which being an "off" phase wherein during this phase the line coupled to the patient is isolated from the hospital's suction line and is instead vented to the ambient atmosphere, and the other phase being an "on" phase, wherein during this phase the line coupled to the patient is provided with a regulated level of suction, e.g., 200 mm Hg., the regulated suction being limited to a level significantly below the level of partial vacuum provided from the source of partial vacuum, e.g., the hospital's suction line;

FIG. 9 is an enlarged partial sectional view of the suction regulator shown in FIG. 6 demonstrating its "off" phase of the intermittent mode of operation;

FIG. 10 is an enlarged partial sectional view of the suction regulator shown in FIG. 8 demonstrating its "on" phase of the intermittent mode of operation;

FIG. 11 is an enlarged partial sectional view of the regulator shown in FIG. 1 showing a detent mechanism and associated interlock for holding the regulator in its various modes of operation and for preventing the regulator from accidentally being switched into its LINE mode of operation; and FIG. 12 is an enlarged view of the portion of the device shown within the circle identified by the reference number 12 in FIG. 11.

DETAILED DESCRIPTION OF THE PREFERRED EMBODIMENTS

Referring now to the drawings wherein like characters refer to like parts there is shown one exemplary embodiment of a suction regulator 20 constructed in accordance with this invention for connection to a source of partial vacuum, e.g., a hospital suction line (not shown) to apply suction when desired and in a manner desired to a patient circuit to which the regulator is connected. The suction regulator 20 has four discrete modes of operation, which will be described in considerable detail later.

In the exemplary embodiment shown herein the regulator 20 is connected to a patient circuit in the form of a patient fluid drainage system 10 (FIG. 2). That patient circuit includes a gastrointestinal drainage tube 12 connected to a fluid collection container 14 via a conduit 16A. A leg of a patient connection line or conduit 16B is provided for drawing a partial vacuum from the container 14. The conduit 16B is connected to the regulator 20 that, in turn, is connected via conduit 18 to a source of partial vacuum, e.g., the hospital's suction line.

It must be pointed out at this juncture that the exemplary regulator 20 (or any other regulator constructed in accordance with this invention) can be used in other applications than that shown in FIG. 2.

The suction regulator 20 is best seen in FIGS. 1, 9 and 10 and basically comprises a housing 22, a control valve 24, a dashpot assembly 26, a regulator knob 28, and a gauge 30. A control valve knob 32, is mounted on the housing and coupled to the control valve. The control valve is constructed in a manner similar to that disclosed in the foregoing U.S. Pat. No. 6,228,056. Thus, it includes a spring-biased piston 34 (FIGS. 9 and 10), an associated diaphragm 36, a control valve stem 38, a spool 40, a pair of magnets 42 and 44. The magnet 42 is mounted on the piston 34 and the magnet 44 is mounted on the spool 40. The piston is biased by a compression spring 46. The control valve also includes a timing mechanism 48 includes an adjustable screw and an associated air inlet port or timing vent 50. The housing includes a body having a suction line port 52, a vent port 54, and a patient line port 56.

The suction line port 52 serves as the means to which the conduit or line 18 from a source of partial vacuum, e.g., the hospital's suction line, may be connected to the regulator 20. The patient line port 56 includes a connector 58 for connection to the conduit 16B. In the exemplary embodiment of the system shown in FIG. 1, the conduit 16 is connected to the container 14 for receiving withdrawn fluid from the patient. To that end the container 14 is connected via another conduit or line 16A to a perforated tube 12 for disposition within the stomach of the patient.

The regulator 20 is arranged to be operated in one of four discrete modes of operation. The first mode of operation is denoted as the "OFF" mode and is established by rotating the control valve knob to a position wherein indicia bearing the word "OFF" are aligned with a mark (indicium) 60 (FIG. 1) on the housing. When the control valve knob is in this position the line 16A to the patient will be isolated from the hospital's suction line and will, instead, be vented to the ambient atmosphere via the vent port 54. The structure and operation of the components making up the regulator for establishing the "OFF" mode of operation will be described later with respect to FIG. 3.

Figure 4:
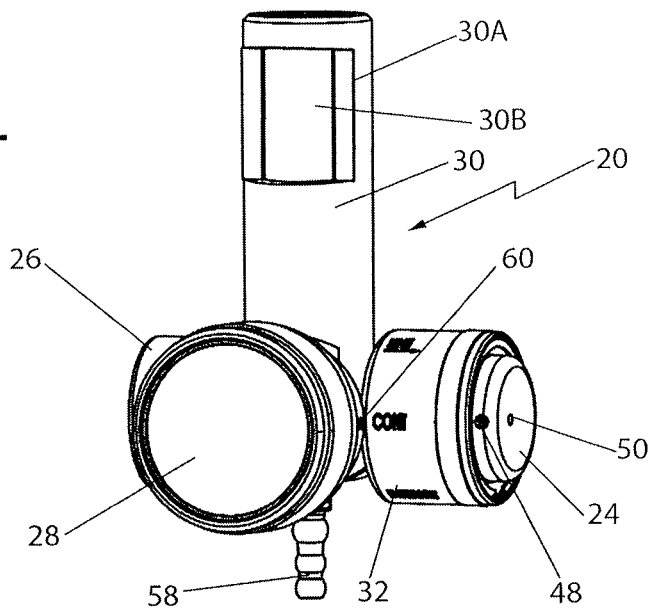
FIG. 4 is a reduced isometric view of the suction regulator of FIG. 1 shown in its continuous ("CONT") mode of operation, wherein continuous regulated suction is provided to the line coupled to the patient, with the continuous regulated suction being limited to a level significantly below the level of partial vacuum provided from the source of partial vacuum e.g., the hospital's suction line.

The second mode of operation is denoted as the "CONT" (abbreviation for "continuous") mode of operation. The continuous mode of operation is established by rotating the control valve knob 30 to a position shown in FIG. 4 wherein indicia bearing the letters "CONT" are aligned with the mark 60 on the housing. When the control valve knob is in this position there will be a regulated level of suction provided to the patient line port 56 by the regulator 20 as long as the regulator is in this mode of operation. The regulated level of suction can be varied and is established by the setting (i.e., rotary position) of the regulator knob 32. To that end, the regulator knob is coupled to a regulator stem (to be described later) which cooperates with an adjustable size regulator port 62 located in the housing. The size of the regulator port is adjusted by the setting of the regulator knob 32 which moves the regulator stem with respect to the port 62 to adjust the amount of suction applied through that port. In typical operation the level of suction provided in the continuous mode of operation is between 0 and approximately 200 mm Hg. The structure and operation of the components making up the regulator for establishing the "CONT" mode will be described later with respect to FIG. 5.

The gauge 30 serves to display the amount of suction being applied to the patient when the regulator is in any operative mode. In the exemplary embodiment of the regulator shown, it is constructed similarly to that disclosed in U.S. Pat. No. 5,992,239, which is also assigned to the same assignee as this invention and whose disclosure is also specifically incorporated by reference herein. It should be pointed out that other types of gauges can be used in lieu of the gauge 30.

As best seen in FIG. 1, the exemplary gauge 30 basically comprises a cylindrical body member having a window 30A, in which a movable (reciprocable) piston 30B is located. The window includes indicia in the form of a plurality of lines (not shown) and a background of discrete color bands of red, orange, yellow and green (not shown), which serve to indicate the level of suction provided by the regulator. In particular, the band of red appears in the background at the bottom of the window 30A, with the band of orange above it and with the band of yellow above the band of orange. The band of green is located above the band of yellow. The piston is of a contrasting color, e.g., is white, to enable the viewer to readily see the level of suction provided against the colored background. In particular depending upon the level of suction provided, the piston will move up or down in the window in front of the indicia and colored background to the position where top end of the white piston will be adjacent and expose a line indicting the particular level of suction applied. In addition, the color band of the background above the top of the piston will be exposed so that a visual indication of the suction will be readily apparent to users. The piston is coupled via a passageway (not shown) to a threaded connector 108 (FIG. 11) in the body of the housing. The level of suction applied by the regulator appears at connector 108 to control the position of the gauge's piston.

The third mode of operation is denoted as the "INTERMIT" (abbreviation for "intermittent") mode of operation. The intermittent mode of operation is established by rotating the control valve knob 32 to a position shown in FIG. 8 wherein indicia bearing the letters "INTERMIT" are aligned with the mark 60 on the housing 22. When the control valve knob is in this position there will also be a regulated level of suction provided to the patient line port 56 by the regulator. However, that regulated suction will be provided intermittently or cyclically. By this it is meant during each cycle of intermittent operation there will be an "on" phase at which time the regulated level of suction will be applied to the patient line, and an "off" phase at which time the patient line will be vented to the ambient atmosphere. In clinical operation the typical duty cycle of each cycle of intermittent operation will be that the "on" phase is approximately twice as long as the "off" phase. For example, the "on" phase can be from 16-20 seconds in duration, while the "off" phase is from 8-10 seconds in duration. The timing of the intermittent mode operation is established by the setting of the timing screw 48 of the timing mechanism, whereupon the rate of flow of air into inlet port 50 and through the timing mechanism is established. As discussed in detail in U.S. Pat. No. 6,228,056 the amount of air flowing through the timing mechanism controls the movement (reciprocation) of the piston and its associated components (e.g., the spool) of the control valve, thereby establishing the duty cycle of intermittent operation. The fluid flow paths, e.g., suction and air, through the regulator during its intermittent mode of operation are shown by the line designated with arrowheads in FIGS. 9 and 10. Those fluid flow paths are discussed in much greater detail in U.S. Pat. No. 6,228,056.

The dashpot assembly 26 serves to dampen the reciprocation of the spool when the regulator is operating in the intermittent mode. To that end, it includes a piston 64 that is disposed in a hollow portion 66 of the housing opposite to the control valve knob 32. The piston is mounted on the end of the spool 40. The structure and operation of the components making up the regulator for establishing the two phases of the intermittent mode will be described later with respect to FIGS. 9 and 10.

The fourth mode of operation is denoted as the "LINE" mode of operation. The LINE mode of operation is established by rotating the control valve knob 32 to a position shown in FIG. 6 wherein indicia bearing the word "LINE" are aligned with the mark 60 on the housing 22. When the control valve knob is in this position the full level of suction available from the source of partial vacuum, e.g., the hospital suction line, will be provided to the patient line port 56 by the regulator 20. The structure and operation of the components making up the regulator for establishing the "LINE" mode will be described later with respect to FIG. 7.

Figure 3:
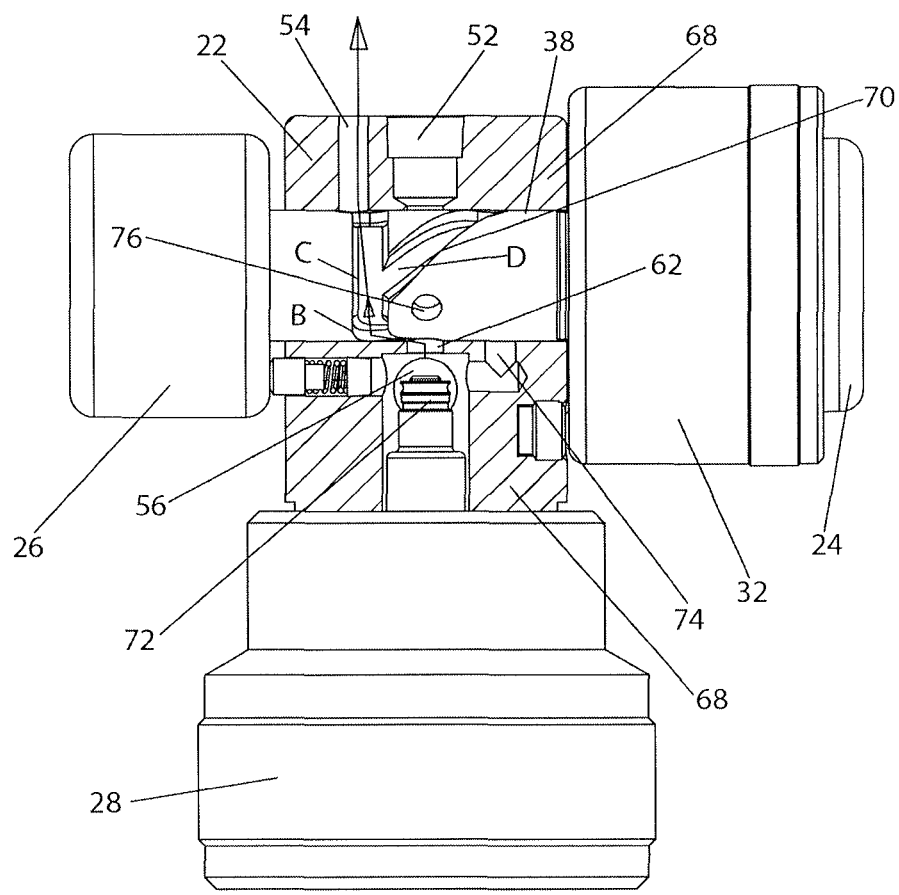
FIG. 3 is an enlarged partial sectional view of the suction regulator of FIG. 1, shown in its "OFF" mode of operation, wherein the line coupled to the patient is isolated from the hospital's suction line so that the line to the patient is at ambient atmospheric pressure.

Attention is now directed to FIG. 3 where the details of the regulator 20 for establishing the "OFF" mode will now be discussed. To that end, as can be seen the housing 22 includes a body portion 68 through which the control valve stem 38 passes. The stem 38 includes a multi-segmented slot 70 in its outer periphery. The slot includes short transversely extending segment A (FIG. 5), a contiguous arcuate segment B (FIGS. 3 and 5), a contiguous long transversely extending segment C (FIGS. 3 and 5), a contiguous angularly extending segment D (FIG. 3) extending from approximately the midpoint of the segment C, and a very short longitudinally extending segment (not shown) at the end of segment C opposite segment B. When the control valve knob is in the OFF position the slot segment A is in fluid communication with the regulated port 62 and a portion of the slot segment C is in fluid communication with the vent port 54. Accordingly, there will be a fluid path as designated by the line bearing the arrowheads from the patient's conduit 16B via connector 58, patient line port 56, regulated port 62, slot portion A, slot portion B, and slot portion C to the vent port 54. It is through this path that air can flow, so that the patient's line will be vented to the ambient atmosphere and at the ambient pressure. Moreover, when the control knob is in the "OFF" position a portion of the periphery of the control valve stem 38 adjacent the slot segments C and D blocks the suction port 52, thereby isolating the hospital's suction line from the patient.

Figure 5:
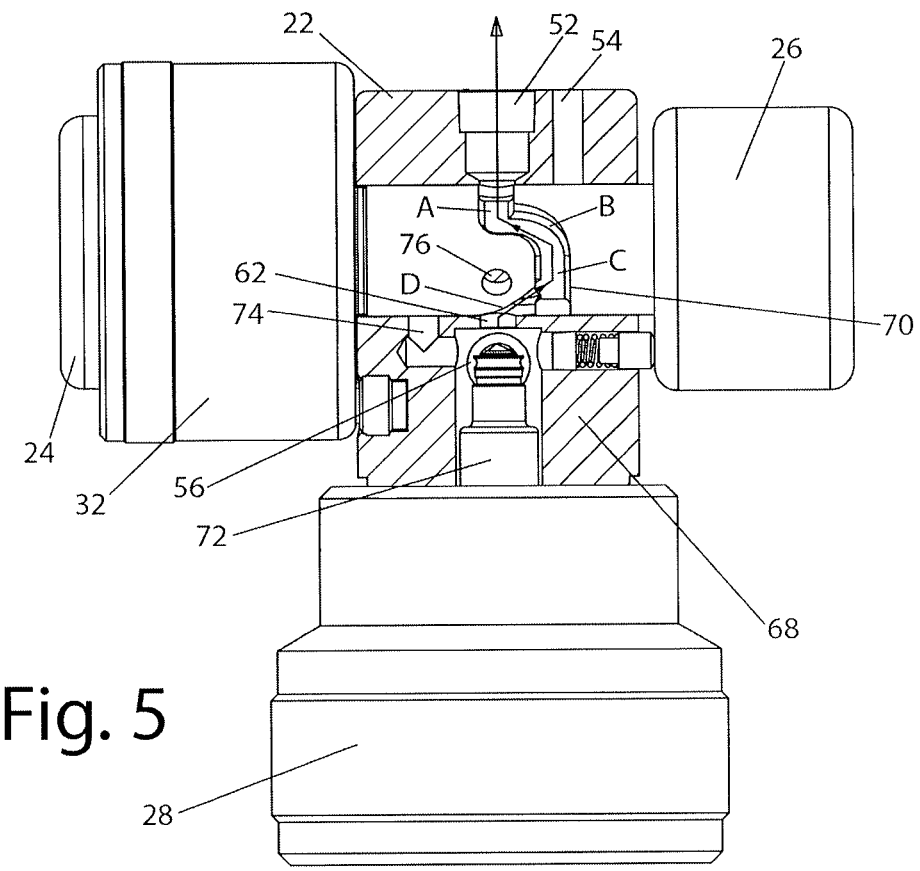
FIG. 5 is an enlarged partial sectional view of the suction regulator shown in FIG. 4 demonstrating its continuous mode of operation.

Operation of the regulator in the continuous ("CONT") regulated mode will now be described with reference to FIG. 5. In this mode the control knob is rotated to the position shown in FIG. 4 so that an angularly extending slot segment D will be in fluid communication with the regulated port 62, while the slot segment A will be in fluid communication with the suction line port 52. Accordingly, there will be a fluid path as designated by the line bearing the arrowheads from the patient's conduit 16B via connector 58, port 56, regulated port 62, slot segment D, slot segment C, slot segment B and slot segment A to the suction line port 52. Thus, the patient's line or conduit will be at a vacuum/suction level established by the setting of the regulator knob 28. As noted earlier the setting of the regulator knob 28 adjusts the amount of suction applied through the regulated port 62. That action is achieved by the movable regulator stem 72 which is coupled to the regulator knob so that it can be brought closer to or further away from the port 62 by rotation of the knob.

Figure 7:
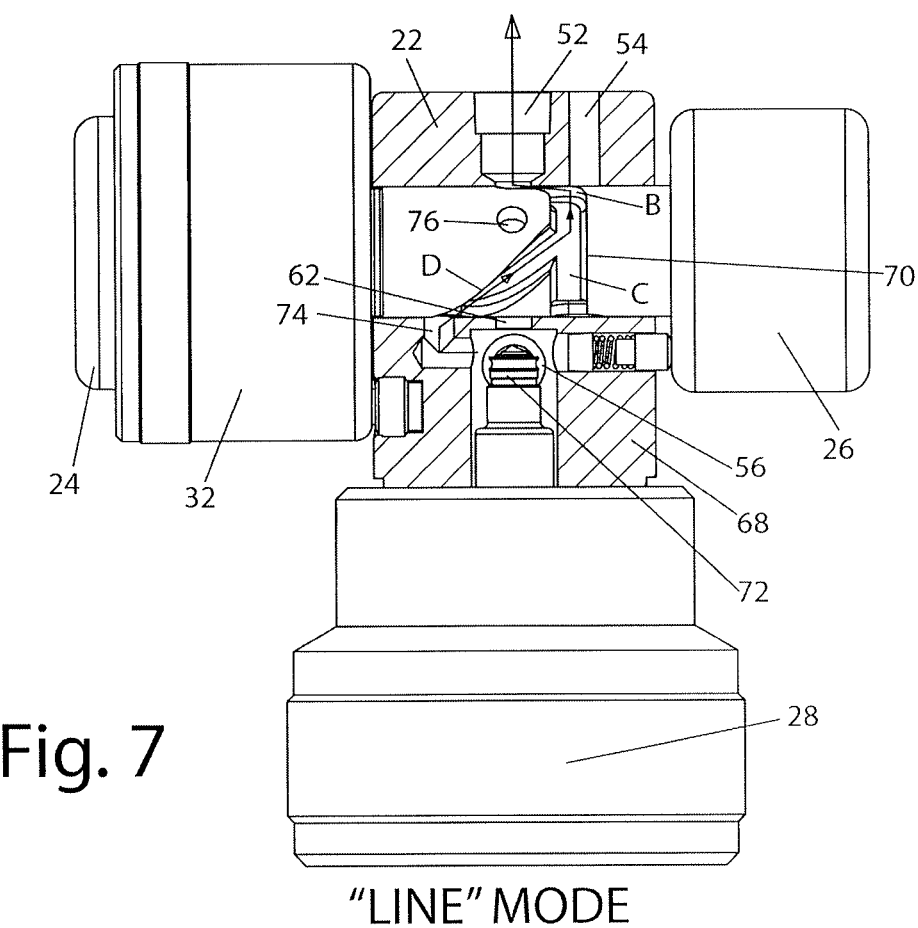
FIG. 7 is an enlarged partial sectional view of the suction regulator shown in FIG. 6 demonstrating its "LINE" mode of operation.

Operation of the regulator in the unregulated line vacuum mode (the "LINE" mode) will now be described with reference to FIG. 7. In this mode the control knob 32 is rotated to the position shown in FIG. 6 so that the portion of the control valve stem 38 adjacent slot segments C and D blocks the regulated port 62 and the slot segment A will be in fluid communication with the suction line port 52. Accordingly, there will be a fluid path as designated by the line bearing the arrowheads from the patient's conduit 16B via connector 58, port 56, an unregulated (i.e., fixed size) port 74 in the body portion 68, through slot segment D, slot segment C, slot segment B and slot segment A to the suction line port 52. Thus, the patient's line or conduit I 6B will be at a vacuum/suction level of the hospital's vacuum supply.

Operation of the regulator in the intermittent ("INTERMIT") regulated mode will now be described with reference to FIGS. 8, 9 and 10. As mentioned above in this mode of operation, each duty cycle has two phases, i.e., the "off" phase wherein the patient's line is vented to the ambient atmosphere, and the "on" phase wherein the patient's line is provided with regulated suction at the level established by the setting of the regulator knob 28. The position and arrangement of the components of the regulator in the "off" phase is shown in FIG. 9. Thus, as can be seen in this phase the spring biased piston 34 of the regulator is in its up or fully retracted position (shown to the right in FIG. 9) under the bias provided by the spring 46, whereupon the spool 40 coupled to the piston is in the position wherein the regulated port 62 is in fluid communication with a hole or aperture 76 in the control valve stem 38. The spool 40 also includes an annular recess or slot 78 in its periphery and which is in fluid communication with the hole 76. The stem 38 includes two other holes, one of which is designated 80. The hole 80 is also in fluid communication with annular recess 78 and with the vent port 54 when the spool is in the position shown in FIG. 9. Accordingly, the patient's conduit or line 16B during the "off" phase of the intermittent duty cycle will be vented to the ambient atmosphere.

Movement of the piston to the down position (left position shown in FIG. 10) under the control of the timing mechanism 48 to the state shown in FIG. 10 results in the establishment of the "on" phase of the intermittent duty cycle. During this phase the spool 40 of the regulator will be moved to the up (right) position shown in FIG. 10 by the operation of the magnets 42 and 44 as set forth in detail in U.S. Pat. No. 6,228,056, whereupon a hole or aperture 76 in the control valve stem 38 will be in fluid communication with the annular slot 78 in the spool 40. The control valve stem includes another hole or aperture 82 which is also in fluid communication with the annular slot 78 in the stem 38. Moreover, the hole 82 is in fluid communication with a longitudinally extending slot 84 in the outer surface of the stem 38, which in turn is in fluid communication with the suction line port 52. Accordingly, the patient's conduit or line 16B during the "on" phase of the intermittent duty cycle will be at the suction level as established by the regulated port 62. The regulator 20 will continue to cycle through its on-off duty cycle for as long as it remains set in the continuous regulated mode, i.e., the control valve knob is in the "INTERMIT" position.

As best seen in FIGS. 11 and 12 the regulator includes a detent mechanism to ensure that when the control valve knob 32 is rotated to any of the "OFF", "INTERMIT" and "CONT" positions it is held in that selected position to prevent accidental displacement therefrom. In particular, a portion of the body of the housing 22 includes a bore 86 in which a compression spring 88 is disposed. The opposite end of the compression spring is located in a counter bore 90 in a detent plunger 92. The distal end of the plunger is tapered slightly at 94. The plunger is retained in the body of the housing by a retainer sleeve 96. The inner surface of the control knob 32 confronting the plunger 92 includes an arcuate slot or recess 98. That slot forms an arc segment of a circle whose center is on the longitudinal axis about which the knob 32 is rotated. Three dimpled concave recesses (only one of which 100 can be seen) are provided at spaced locations along the arcuate recess 98. The dimpled recesses are located in the arcuate recess 98 at respective ones of the "OFF", "INTERMIT" and "CONT" positions. Hence, when the control valve knob 32 is rotated to any of those positions the tapered end 94 of the detent plunger 92 will snap fit into the associated dimpled recess 100 under the bias force provided by the compression spring 88, thereby holding the control valve knob in that position.

Notwithstanding the operation of the detent mechanism to hold the control knob in any one of the "OFF", "INTERMIT" and "CONT" positions, the regulator 20 is preferably arranged to prevent that knob from being rotated to the "LINE" position to ensure that the regulator cannot be accidentally placed in the "LINE" mode. To that end, the regulator includes an interlock associated with the detent mechanism. In particular, the interlock includes a ledge 102 located at one end of the arcuate recess 98. The bottom surface of the arcuate recess at the ledge 102 is disposed above the bottom surface of the portion of the arcuate recess where the dimpled recesses 100 are located. Thus, the portion of the arcuate recess 98 containing the dimpled recesses 100 is deeper than the portion of the arcuate recess at the ledge 102. The end of the shallower (ledge) portion of the arcuate recess 98 serves as a stop which defines the "LINE" position for the control knob 32. The control knob 32 is arranged to be pulled or moved outward in the direction of the arrow shown in FIG. 11 in order to overcome the interlock to rotate the control knob to the "LINE" position. Thus, in order to rotate the control knob to the "LINE" position one has to pull outward on the control knob in the direction of the arrow in FIG. 11 to free the tapered end 94 of the plunger from the deeper portion of the arcuate recess, and bring the plunger onto the arcuate slot portion defined by the ledge 102, whereupon the control knob 32 can be rotated to move the plunger down the ledge to bring it to the end of that recess portion, i.e., to the "LINE" position. This establishes the line mode of operation, a setting that cannot be accidentally achieved. The control knob 32 is normally biased in its "in" position by a plunger 104 located in a bore in the body 68 biased by a spring 106. This bias tends to prevent the control knob from being accidentally pulled out to rotate to the "LINE" position.

To return the regulator from the line position to any one of the "OFF", "CONT" or "INTERMIT" positions all that is required is to rotate the control knob in the opposite direction to cause the tapered end of the plunger to slide off of the ledge portion of the arcuate slot 98 and into the deeper portion of that slot. The knob can then be rotated to bring the plunger 92 into alignment with any of the dimpled recesses 100 at the desired mode of operation position.

Without further elaboration the foregoing will so fully illustrate our invention that others may, by applying current or future knowledge, adopt the same for use under various conditions of service.

We claim:

1. A regulator for use in regulating suction provided via a line to a patient, said regulator comprising a housing having an inlet, and an outlet, said inlet being arranged to be coupled to a source of partial vacuum, said outlet being arranged to be coupled to a patient circuit, said regulator being arranged for operating in any one of four discrete modes of operation, a first one of said four discrete modes of operation isolating the source of partial vacuum from the patient circuit, a second one of said four discrete modes of operation providing continuous regulated suction to the patient circuit, said continuous regulated suction being limited to a level below the level of partial vacuum provided from the source of partial vacuum, a third one of said four discrete modes of operation providing intermittent regulated suction to the patient circuit, said intermittent regulated suction being limited to a level below the level of partial vacuum provided from the source of partial vacuum, a fourth of said four discrete modes of operation providing continuous full suction to the patient circuit, said continuous full suction being at the level of suction provided by said source of partial vacuum.

2. The suction regulator of claim 1 wherein said regulator includes a control member arranged to be moved to respective first, second, third and fourth positions, said first position corresponding to said first of said four discrete modes of operation, said second position corresponding to said second of said four discrete modes of operation, said third position corresponding to said third of said four discrete modes of operation, and said fourth position corresponding to said fourth of said four discrete modes of operation, whereupon said regulator operates in the mode of operation associated with the position to which said control portion is moved.

3. The suction regulator of claim 2 wherein said regulator additionally comprises an interlock arranged to prevent said control member from being accidentally moved to said fourth position.

4. The suction regulator of claim 3 additionally comprising a detent mechanism to releasably hold said control member in any one of said first, second or third positions.

5. The suction regulator of claim 4 wherein said detent mechanism comprises a spring biased plunger and a plurality of recesses, each of said recesses being arranged to receive said spring biased plunger to establish a respective one of said first, second, and third positions.

6. The suction regulator of claim 3 wherein said interlock comprises an arcuate recess and a spring biased plunger, said arcuate recess having a first portion of a first depth and a second portion of a second depth, said first depth being greater than said second depth, said spring biased plunger being located in said first portion of said arcuate recess when said control member is in one of said first, second or third positions, said control member being arranged to be pulled away from said housing to enable said spring biased plunger to be located in said second portion of said arcuate recess at said fourth position.

7. The suction regulator of claim 6 wherein said control member comprises a rotatable knob.

8. The suction regulator of claim 7 wherein said rotatable knob is spring biased to resist being pulled away from said housing.

9. The suction regulator of claim 2 wherein said control member comprises a rotatable knob.

10. The suction regulator of claim 2 additionally comprising a detent mechanism to releasably hold said control member in any one of said first, second or third positions.

11. The suction regulator of claim 10 wherein said detent mechanism comprises a spring biased plunger and a plurality of recesses, each of said recesses being arranged to receive said spring biased plunger to establish a respective one of said first, second, and third positions.

12. The suction regulator of claim 2 wherein the patient circuit is arranged for withdrawing body fluids from a patient and wherein said outlet is arranged to be coupled to a container for receipt of body fluids from the patient.

13. The suction regulator of claim 1, wherein said regulator is arranged for adjusting the level of said continuous regulated suction to a desired level below the level of partial vacuum provided from said source of partial vacuum.

14. The suction regulator of claim 13, wherein said regulator is arranged for adjusting the level of said intermittent regulated suction to a desired level below the level of partial vacuum provided from said source of partial vacuum.

15. The suction regulator of claim 13 additionally comprising a gauge to provide a visual indication of the level of said continuous regulated suction.

16. The suction regulator of claim 1, wherein said regulator is arranged for adjusting the level of said intermittent regulated suction to a desired level below the level of partial vacuum provided from said source of partial vacuum.

17. The suction regulator of claim 16 wherein said intermittent mode of operation comprises an "on" phase during which regulated suction at a desired level below the level of partial vacuum provided from said source of partial vacuum is delivered to the line to the patient and an "off" phase during time the source of partial vacuum is isolated from the line to the patient and that line is vented to the ambient atmosphere, said regulator being adjustable to establish the duration of said "on" and "off" phases.

18. The suction regulator of claim 16 additionally comprising a gauge to provide a visual indication of the level of said intermittent regulated suction.

19. The suction regulator of claim 1 wherein said intermittent mode of operation comprises an "on" phase during which regulated suction at a desired level below the level of partial vacuum provided from said source of partial vacuum is delivered to the line to the patient and an "off" phase during which the source of partial vacuum is isolated from the line to the patient and that line is vented to the ambient atmosphere, said regulator being adjustable to establish the duration of said "on" and "off" phases.

20. The suction regulator of claim 1 wherein the patient circuit is arranged for withdrawing body fluids from a patient and wherein said outlet is arranged to be coupled to a container for receipt of body fluids from the patient.

* * * * *